(12) United States Patent
Legendre et al.

(10) Patent No.: US 8,165,825 B2
(45) Date of Patent: Apr. 24, 2012

(54) METHOD FOR ELECTROMAGNETICALLY MEASURING PHYSICAL PARAMETERS OF A PIPE

(75) Inventors: Emmanuel Legendre, Houston, TX (US); Thilo Brill, Feucherolles (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 546 days.

(21) Appl. No.: 11/912,488

(22) PCT Filed: Apr. 5, 2006

(86) PCT No.: PCT/EP2006/003469
§ 371 (c)(1),
(2), (4) Date: Sep. 28, 2009

(87) PCT Pub. No.: WO2006/114208
PCT Pub. Date: Nov. 2, 2006

(65) Prior Publication Data
US 2010/0017137 A1  Jan. 21, 2010

(30) Foreign Application Priority Data
Apr. 26, 2005 (EP) ..................................... 05290929

(51) Int. Cl.
*G01B 5/28* (2006.01)

(52) U.S. Cl. .............................. 702/34; 702/38; 324/221
(58) Field of Classification Search ................... 702/6, 7, 702/11, 34–36, 38; 324/220, 221; 175/45
See application file for complete search history.

(56) References Cited

U.S. PATENT DOCUMENTS

| | | | |
|---|---|---|---|
| 2,992,390 A | | 7/1961 | De Witte |
| 4,292,588 A | * | 9/1981 | Smith .......................... 324/221 |
| 4,292,589 A | | 9/1981 | Bonner et al. |
| 4,546,314 A | | 10/1985 | Minerbo et al. |
| 2002/0043973 A1 | | 4/2002 | Amini et al. |
| 2003/0051914 A1 | | 3/2003 | Bittar |

FOREIGN PATENT DOCUMENTS
EP  0816838  1/1998

* cited by examiner

*Primary Examiner* — Manuel L Barbee
(74) *Attorney, Agent, or Firm* — Matthias Abrell (57) ABSTRACT

The invention discloses a method for electromagnetically measuring physical parameters of a pipe that includes measuring a pipe inner diameter ID and a pipe ratio of magnetic permeability to electrical conductivity $\mu 2/\sigma 2$ by means of a measuring arrangement 1 comprising a transmitter coil 2 and a receiver coil 3, both coils being coaxial to and longitudinally spaced from each other, the measuring arrangement being adapted to be positioned into the pipe CS and displaced through the pipe.

6 Claims, 4 Drawing Sheets

METHOD FOR ELECTROMAGNETICALLY MEASURING PHYSICAL PARAMETERS OF A PIPE

FIELD OF THE INVENTION

The invention relates to a method for electromagnetically measuring physical parameters of a pipe. The physical parameters are the ratio of magnetic permeability to electrical conductivity and/or the inner diameter of the pipe.

The invention is particularly well suited for implementation by a non-destructive electromagnetic inspection tool run into a ferromagnetic pipe.

The invention is particularly well designed for applications in the oilfield industry.

BACKGROUND OF THE INVENTION

Figure 1:
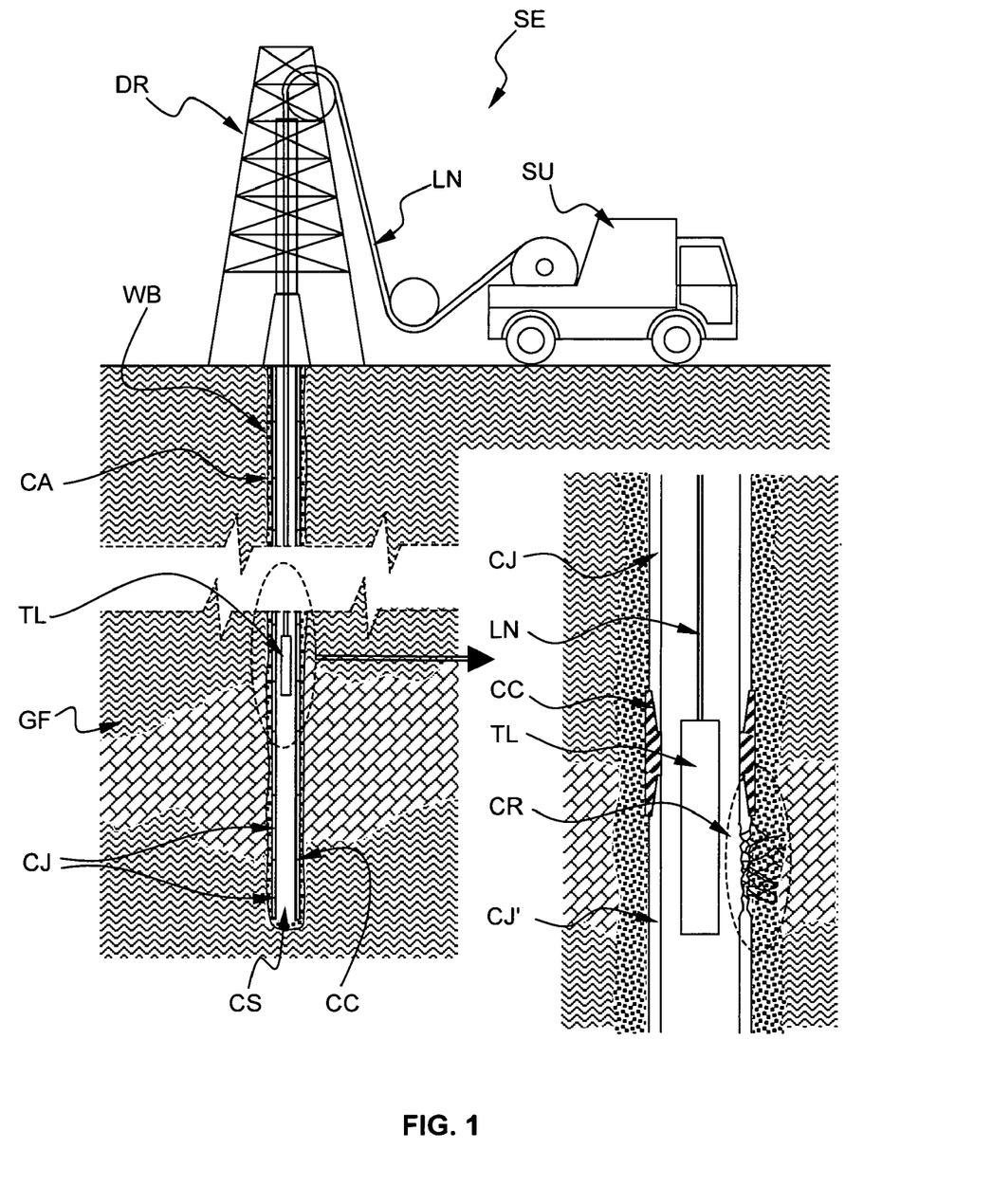
FIG. 1 schematically shows a typical onshore hydrocarbon well location and an enlarged portion of a zone where measurements are performed.

FIG. 1 schematically shows a typical onshore hydrocarbon well location and surface equipments SE above a hydrocarbon geological formation GE after a well-bore WB drilling operation has been carried out, after a casing string CS has been run and after cementing operations have been carried out for sealing the annulus CA (i.e. the space between the well-bore WB and the casing string CS).

Typically, the casing string CS comprises a plurality of casing joints CJ, two casing joints being coupled together by a casing collar CC. The casing string function is to stabilize the well-bore.

The casing joint CJ is a length of steel pipe, generally around 13 m or 40 ft long with an externally threaded (male thread form) connection at each end. Casing joints are assembled to form a casing string of the correct length and specification for the well-bore in which it is installed.

The casing collar CC is an internally threaded (female thread form) short length of pipe used to connect two casing joints. The resulting connection must provide adequate mechanical strength to enable the casing string to be run and cemented in place. The casing collar must also provide sufficient hydraulic isolation under the design conditions determined by internal and external pressure conditions and fluid characteristics.

The casing may be made of plain carbon steel, stainless steel or other material in order to withstand a variety of forces, such as collapse, burst, and tensile failure, as well as chemically aggressive fluid. Nevertheless, in harsh environment, the casing may be subject to corrosion that may affect its functionality.

At this stage, well logging operation may be carried out. The well logging operation serves to measure various parameters of the hydrocarbon well geological formation (e.g. resistivity, porosity, etc. . . . at different depths) and in the well-bore (e.g. temperature, pressure, fluid type, fluid flowrate, etc. . . . at different depths). Such measurements are performed by a logging tool TL. Generally, a logging tool comprises at least one sensor (e.g. resistivity sonde, mechanical sonde, gamma ray neutron sonde, accelerometer, pressure sensor temperature sensor, etc. . . . ) and measures at least one parameter. It may include a plurality of same or different sensors sensitive to one or more parameters. The logging tool is moved up and down in the borehole for gathering data about the various parameters by means of a cable LN. The cable may be a mechanical cable, an electrical cable or an electro-optical cable comprising a fiber line protected against potential harsh environment existing in the well-bore. The mechanical, electrical, or electro-optical cable transmits electrical signals or optical signals from the logging tool to the surface unit.

The logging tool may be deployed inside the well-bore by an adapted surface equipment SE that may include a vehicle SU and an adapted deploying system, e.g. a drilling rig DR or the like. Data related to the hydrocarbon geological formation GF or to the well-bore WB gathered by the logging tool TL may be transmitted in real-time to the surface, for example to the vehicle fitted with an appropriate data collection and analysis computer and software.

In particular, a logging tool TL may comprise an inspection tool.

FIG. 1 also schematically shows a magnified view of a portion of the cased well-bore, wherein the tool TL comprises an inspection tool. The inspection tool can detect the position shape and dimension of a corrosion zone CR affecting a casing joint CJ'. The tool TL provides the measurements to the surface equipment through the connection line LN. By correlating this detection with depth measurements made by the tool TL, it is possible to run an appropriate tool down-hole for providing an appropriate remedial treatment (e.g. chemical treatment, patch, casing replacement or the like) for consolidating the corroded casing joint CJ'.

The inspection tool may be a mechanical caliper, an ultrasonic tool or an electromagnetic tool.

The mechanical caliper comprises a plurality of fingers for sensing the inner geometry of the casing. The mechanical calipers cannot be used for the determination of casing thickness, cannot distinguish non-metallic deposits on the casing from the metallic casing itself, and may initiate corrosion by scratching the casing surface.

The ultrasonic tool measures the time-of-flight of a sound-pulse between emission by the tool, reflections at the inner and outer surfaces of the casing and reception by the sound-wave detectors in the tool. They may measure the inside diameter as well as the thickness of the casing. The ultrasonic tool cannot be used when the casing transports a fluid mixture comprising a certain quantity of gas relatively to liquid, and provides deteriorated reflected signals in the presence of surface roughness which typically arise in corroded casing.

The electromagnetic tool is a non-destructive inspection tool. It may be based on either the flux-leakage principle, or the eddy-current principle or a combination thereof. The electromagnetic tool is insensitive to non-conductive deposits and can operate irrespective of the nature of the fluid mixture flowing into the casing.

The electromagnetic tool based on flux-leakage principle is typically used for the detection of localized damages in a ferromagnetic casing. This tool commonly subjects the casing to a strong static magnetic field. Due to the ferromagnetic nature of the casing, the magnetic return flux is mainly confined to the inside of the metal casing. In the presence of discontinuities in the metal, such as pits and holes caused by corrosion, the magnetic flux "leaks" out of the metal casing and may be detected with appropriate magnetic sensors such as coils, Hall probes, or magneto-resistive sensors. To allow for sufficiently sensitive and quantitative measurements, the flux-leakage based tool requires strong magnetic fields and good flux coupling into the inspected casing. This implies close proximity of the magnetic field source to the inner casing surface. The combinations of casings and tubings used in hydrocarbon wells often exhibit varying casing diameters that render the requirements of sufficiently strong and well-coupled magnetic flux difficult to maintain.

The electromagnetic tool based on eddy-current principle is well-suited for the measurement of both, inside diameter and wail thickness of ferromagnetic metallic casing. This tool excites an alternating current in a coil transmitter adapted for inducing eddy-currents in the surrounding conductive casing and measures the induced voltage in a separate receiver coil. Alternatively, the tool may measure the impedance of the transmitter coil. The transimpedance is affected by the casing magnetic permeability ($\mu$) electrical conductivity ($\sigma$) and the inner diameter of the nearby casing. In the case of electromagnetic tool where sufficiently low frequencies and large coil separations are used, measurement of the transimpedance is used to extract the ratio of wall thickness d of the casing to skin depth $\delta$, the so-called electromagnetic thickness d/$\delta$.

It is well known that the results for inner diameter and wall thickness have to be corrected particularly for variations in magnetic permeability which can be significant, for instance due to mechanical stress or heat exposure. Document U.S. Pat. No. 4,546,314 proposes a first order correction method. However, in practice, it has been found that this first-order correction is commonly insufficient in order to achieve satisfactory measurements accuracy.

SUMMARY OF THE INVENTION

One goal of the invention is to propose a method for measuring physical parameters of a pipe, namely the inner diameter of the pipe and/or the ratio of magnetic permeability to electrical conductivity of the pipe which overcomes the drawbacks of the prior art measuring methods.

According to a first aspect, the invention relates to a method for electromagnetically measuring physical parameters of a pipe by means of a measuring arrangement comprising a transmitter coil and a receiver coil, both coils being coaxial to and longitudinally spaced from each other, the measuring arrangement being adapted to be positioned into the pipe and displaced through the pipe, the pipe physical parameters being the pipe inner diameter and the pipe ratio of magnetic permeability to electrical conductivity, the method comprising the steps of:

a1) exciting the transmitter coil by means of a transmitter current, the transmitter current having a first excitation frequency, a2) measuring a receiver voltage at the receiver coil, a3) determining a transimpedance between the transmitter coil and the receiver coil based on the transmitter current and the receiver voltage, and determining a measurement ratio based on said transimpedance, b) repeating the excitation step a1), the measuring step a2), the transimpedance and the measurement ratio determination step a3) for at least a second excitation frequency so as to define a measurement ratio vector, c) calculating a prediction function vector based on the first and at least the second excitation frequency, a plurality of potential pipe ratio of magnetic permeability to electrical conductivity and a plurality of potential pipe inner diameter, and d) applying a minimizing algorithm onto the measurement ratio vector and the prediction function vector and determining the pipe inner diameter and the pipe ratio of magnetic permeability to electrical conductivity corresponding to a maximum solution of the algorithm.

The measurement ratio may be determined by calculating the ratio between a real component of the transimpedance and an absolute value of the transimpedance.

Optionally, the method may further comprise the step of performing an air-calibration, and replacing the measurement ratio by a calibrated measurement ratio. The calibrated measurement ratio is determined by calculating the ratio between an imaginary component of an air normalized transimpedance and an absolute value of an air normalized transimpedance.

The prediction function vector may be calculated for a determined measuring arrangement geometry based on a real and dimensionless variable vector proportional to a plurality of potential pipe ratio of magnetic permeability to electrical conductivity and a normalized inverse of the square root of the first and at least the second excitation frequency, and a plurality of potential pipe inner diameter.

According to another aspect, the invention relates to a logging tool for electromagnetically measuring physical parameters of a pipe, the logging tool being adapted to be positioned into the pipe, displaced through the pipe and coupled to a surface equipment. The logging tool comprises a measuring arrangement and an electronic arrangement connected to the measuring arrangement. The measuring arrangement comprises a transmitter coil and a receiver coil, both coils being coaxial to and longitudinally spaced from each other. The electronic arrangement comprises a transmitter circuit for exciting the transmitter coil by means of a transmitter current according to a plurality of excitation frequencies and a receiver circuit for measuring a receiver voltage at the receiver coil. The electronic arrangement further comprises a processing circuit for:

determining a transimpedance between the transmitter coil and the receiver coil based on the transmitter current and the receiver voltage for the plurality of frequencies,     determining a measurement ratio vector based on said transimpedance for the plurality of frequencies,     calculating a prediction function vector based on the plurality of excitation frequencies, a plurality of potential pipe ratio of magnetic permeability to electrical conductivity and a plurality of potential pipe inner diameters, and     applying a minimizing algorithm onto the measurement ratio vector and the prediction function vector and determining the pipe inner diameter and the pipe ratio of magnetic permeability to electrical conductivity corresponding to a maximum solution of the algorithm.

According to still another aspect, the invention relates to a computer program product for a pipe physical parameters measuring arrangement. The computer program product comprising a set of instructions that, when loaded into a program memory of an electronic arrangement coupled to the measuring arrangement, causes the electronic arrangement to carry out the steps of:

determining a transimpedance between the transmitter coil and the receiver coil based on the transmitter current and the receiver voltage for the plurality of frequencies,     determining a measurement ratio vector by calculating the ratio between a real component of the transimpedance and an absolute value of the transimpedance for the plurality of frequencies,     calculating a prediction function vector based on the plurality of excitation frequencies, a plurality of potential pipe ratio of magnetic permeability to electrical conductivity and a plurality of potential pipe inner diameter, and     applying a minimizing algorithm onto the measurement ratio vector and the prediction function vector and determining the pipe inner diameter and the pipe ratio of magnetic permeability to electrical conductivity corresponding to a maximum solution of the algorithm.

The computer program may carry out the step of determining the measurement ratio by calculating the ratio between a real component of the transimpedance and an absolute value of the transimpedance.

Alternatively, the computer program may carry out the step of replacing the measurement ratio by a calibrated measurement ratio determined by calculating the ratio between an imaginary component of an air normalized transimpedance and an absolute value of an air normalized transimpedance when an air-calibration has been performed.

Thus, the invention allows extracting both the inner diameter and the ratio of magnetic permeability to electrical conductivity of the pipe with a great accuracy.

The derived ratio of magnetic permeability to electrical conductivity of the pipe may be used to correct the electromagnetic thickness d/δ measurements so as to render them insensitive to any permeability effect.

BRIEF DESCRIPTION OF THE DRAWINGS

The present invention is illustrated by way of example and not limited to the accompanying figures, in which like references indicate similar elements:

FIG. 2.A is a cross section view into a casing schematically showing the measuring arrangement of the invention;

FIG. 2.B schematically shows the electronic arrangement associated with the measuring arrangement of the invention;

DETAILED DESCRIPTION OF THE INVENTION

Figure 2:
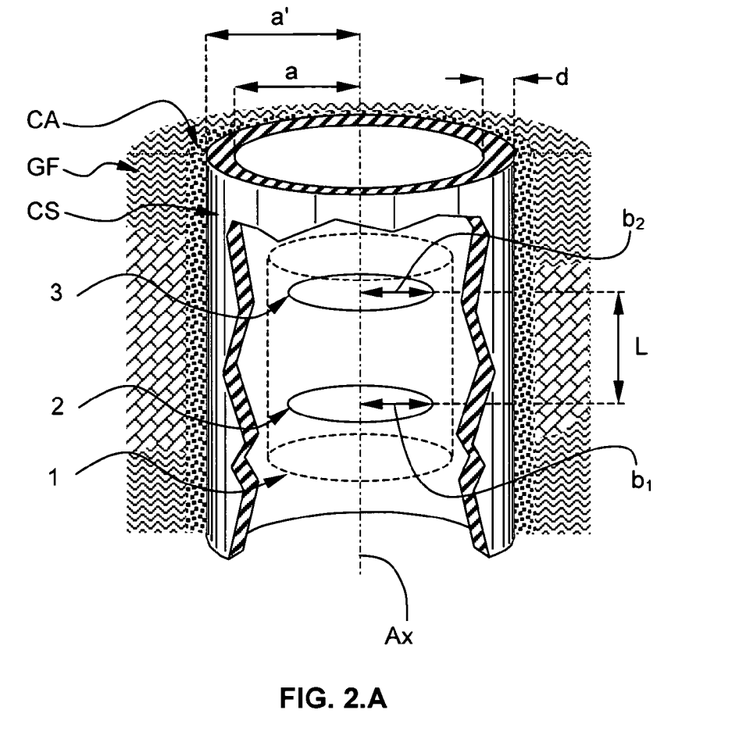

FIG. 2 shows, in a highly diagrammatic manner, the measuring arrangement 1 according to a preferred embodiment of the invention. The measuring arrangement 1 is fitted within the logging tool TL illustrated in FIG. 1. The measuring arrangement 1 comprises a first coaxial coil 2 and a second coaxial coil 3. The first coaxial coil 2 is a transmitter coil having a radius $b_1$. The second coaxial coil 3 is a receiver coil having a radius $b_2$.

The transmitter coil is spaced from the receiver coil by a distance L. Although, each coil is represented as an infinitesimal current loop, it will be apparent for a person skilled in the art that each coil may be a finite size coil. For example, each coil may be constructed by the superposition of individual current loops and comprises a determined number of turns. Advantageously, both coils are coaxial to the central axis Ax of the casing.

The measuring arrangement 1 is inserted within a cemented casing CS.

The casing CS is characterized by its electromagnetic properties, namely a casing magnetic permeability $\mu_2$, a casing electrical conductivity $\sigma_2$ and a casing permittivity $\epsilon_2$. The casing CS is also characterized by its geometry, namely a hollow cylindrical shape. The casing is characterized by an inside radius a and an outside radius a'. The wall thickness d of the casing corresponds to the difference between the outside radius and the inside radius (i.e. d=a'−a).

The medium inside the casing is characterized by its electromagnetic properties, namely an inside medium magnetic permeability $\mu_1$, an inside medium electrical conductivity $\sigma_1$ and an inside medium permittivity $\epsilon_1$. The medium inside the casing may be a multiphase fluid mixture made of, for example, oil, gas and water.

The medium outside the casing is characterized by its electromagnetic properties, namely an outside medium magnetic permeability $\mu_3$, an outside medium electrical conductivity $\sigma_3$ and an outside medium permittivity $\epsilon_3$. The medium outside the casing is the geological formation GF separated from the casing CS by the cemented annulus CA.

FIG. 2.B schematically shows the electronic arrangement EA associated with the measuring arrangement 1 of the invention. Advantageously, the electronic arrangement EA is fitted within the tool TL. The electronic arrangement EA comprises well known circuit associated with electromagnetic tool, namely a transmitter circuit TXC, a receiver circuit RXC, a controller CONT, a digitizing arrangement DIA and a processing circuit PRO.

The transmitter circuit TXC is connected to the transmitter coil 2. The receiver circuit RXC is connected to the receiver coil 3. Both transmitter TXC and receiver RXC circuit are connected to the controller CONT and to the digitizing arrangement DIA. The processing circuit PRO is connected to the controller CONT and the digitizing arrangement DIA. The processing circuit PRO is further coupled to the surface equipment SE.

The transmitter circuit TXC comprises an appropriate oscillator so that the transmitter coil may be excited by a determined transmitter current I and according to a determined excitation frequency $f_i$. The transmitter coil 2 generates an electromagnetic field propagating in the inside medium, within the casing and in the outside medium.

The receiver coil 3 provides a receiver voltage V to the receiver circuit RXC, the receiver voltage being induced by the propagated electromagnetic field. The receiver circuit RXC may comprise a phase locked loop oscillator so that the signal provided by the transmitter coil may be detected. The digitizing arrangement DIA may comprise appropriate amplifier, filter and digitizer for preparing an appropriate signal to be treated by the processing circuit PRO. The processing circuit PRO implements the method of the invention as hereinafter described and eventually sends the results to the surface equipment SE. Alternatively, the processing circuit PRO may send raw measurements to the surface equipment SE, the implementation of the method of the invention being then performed by the processing and computing capabilities of the surface equipment.

The theoretical basis of the invention will be explained hereinafter.

The electromagnetic propagation coefficient k of the electromagnetic fiend within each medium n (n taking the values 1, 2 or 3 corresponding to the medium inside the casing, the casing and the medium outside the casing, respectively) may be defined as:

$$k_n^2 = \epsilon_n \mu_n \omega^2 + i \sigma_n \mu_n \omega \quad (1)$$

where ω=2 πf is the radian frequency of the transmitter current.

When the electromagnetic field is not sufficiently attenuated after traveling through the the casing (medium 2), the electromagnetic field inside the casing may be sensitive to the wall thickness d of the casing and to the medium outside the casing (medium 3). Due to the skin-effect, the attenuation of the electromagnetic fields within the casing (medium 2) can be approximated by exp(−‖$k_2$‖d).

As a consequence, if ‖$k_2$‖d is substantially greater than unity, it is possible to put aside the medium outside the casing (medium 3) in order to simplify the equations. Thus, the problem can be simplified to a two medium problem. The medium inside the casing (medium 1) is a multiphase fluid mixture within the radius r<a. The casing (medium 2) is the metal outside the radius r≧a.

A further simplification relates to the fact that the permittivity term of the metallic casing (medium 2) can typically be neglected for the range of frequencies used in relation with the invention (see examples below), thus, $$k_2^2 \approx i\sigma_2\mu_2\omega \qquad (2)$$

The transimpedance measurement Z is defined as the mutual impedance between the transmitter current I and the receiver voltage V:

$$Z = \frac{V}{I} \qquad (3)$$

When the coils 2 and 3 are centered within the casing, i.e. the coils 2 and 3 are coaxial to the axis Ax, the transimpedance may be defined as:

$$Z = Z_O + Z_P \qquad (4)$$

where $Z_O$ is the transimpedance of the medium inside the casing (medium 1), said medium being a homogenous medium, and is given by:

$$Z_0 = \begin{cases} 2i\omega\mu_1 b_1 b_2 \int_0^\infty d\lambda I_1(\beta_1 b_1) K_1(\beta_1 b_2) \cos(\lambda L), & b_1 \le b_2 \\ 2i\omega\mu_1 b_1 b_2 \int_0^\infty d\lambda I_1(\beta_1 b_2) K_1(\beta_1 b_1) \cos(\lambda L), & b_1 \ge b_2 \end{cases} \qquad (5)$$

and where $Z_P$ is the impedance effects due to the casing (medium 2), and is given by:

$$Z_p = 2i\omega\mu_1 b_1 b_2 \int_0^\infty d\lambda I_1(\beta_1 b_1) I_1(\beta_1 b_2) \Gamma(\lambda) \cos(\lambda L) \qquad (6)$$

where $\beta_n = \sqrt{\lambda^2 - k_n^2}$, and $I_n(x)$, $K_n(x)$ are modified Bessel functions (n taking the values 1 or 2).

In the case of the medium inside the casing (medium 1) is a non-conducting or poorly-conducting medium, i.e. $|k_1 a| \ll 1$, it can be approximated that $\beta_1 = \lambda$ and thus the coupling factor $\Gamma(\lambda)$ can be expressed as:

$$\Gamma(\lambda) = -\frac{K_1(\lambda a) - \lambda a T K_0(\lambda a)}{I_1(\lambda a) + \lambda a T I_0(\lambda a)} \qquad (7)$$

where a dimensionless quantity T is introduced and defined as:

$$T = -\frac{\mu_2}{\mu_1} \frac{1}{\beta_2 a} \frac{K_1(\beta_2 a)}{K_0(\beta_2 a)} \qquad (8)$$

Since in practical cases $\mu_1$ is equal to the known permeability of vacuum $\mu_0$, the dimensionless quantity T only depends on the casing electromagnetic properties and diameter.

For casing having a large casing conductivity $\sigma_2$, the following approximation can be made:

$$\beta_2 \approx -ik_2 \approx (1-i)\sqrt{\frac{\sigma_2\mu_2\omega}{2}} = (1-i)\frac{1}{\delta} \qquad (9)$$

where the quantity δ represents the skin-depth, given by:

$$\delta = \sqrt{\frac{2}{\sigma_2\mu_2\omega}} \qquad (10)$$

Then, the dimensionless quantity T is given by:

$$T \approx -\frac{\mu_2}{\mu_1} \frac{1}{ik_2 a} \frac{K_1(ik_2 a)}{K_0(ik_2 a)} \qquad (11)$$

The dimensionless quantity T can be further simplified, assuming that $|k_2 a| \gg 1$ for the range of frequencies used in relation with the invention (see examples below):

$$T = \frac{1+i}{\sqrt{2}} \frac{\mu_2}{\mu_1} \frac{1}{a\sqrt{\sigma_2\mu_2\omega}} = \sqrt{2}(1+i)\tau \qquad (12)$$

where a real and dimensionless variable τ is introduced and defined as:

$$\tau = \frac{1}{\mu_i\sqrt{\omega}} \frac{1}{ID}\sqrt{\frac{\mu_2}{\sigma_2}} = \frac{1}{\sqrt{2}} \frac{\mu_2}{\mu_1} \frac{\delta}{ID} \qquad (13)$$

where ID=2a is the inner diameter of the casing.

Therefore, a key observation can be made regarding the transimpedance measurement: For the given transmitter coil radius $b_1$, receiver coil radius $b_2$, spacing L and frequency ω, the transimpedance response Z depends only on two physical parameters of the casing namely the ratio of magnetic permeability to electrical conductivity μ/σ and the inner diameter ID of the casing. This is true whatever the frequency used as long as the following three conditions are satisfied:

$$|k_2|d \gg 1 \text{ and } |k_2 a| \gg 1 \text{ and } |k_1 a| \ll 1 \qquad (14)$$

Those conditions are satisfied for common ferromagnetic oil well casings and a frequency larger than about 1 kHz and smaller than about 100 kHz. Further, the conditions imply that the real and dimensionless variable τ is limited to the interval comprised between zero and one, namely [0,1]. Finally, the conditions also imply that the measurement is limited to the so-called "near-field" regime. The near-field regime occurs when the direct coupling between transmitter and receiver—mediated by the thin-skin eddy-current interaction—dominates the transimpedance.

According to the invention, a measurement ratio M is defined as:

$$M = -\frac{\text{Re}(V/I)}{\text{Abs}(V/I)} \qquad (15)$$

Preferably, an air-calibration is performed. The measurement ratio M can be seen as the sum of a casing response and an air response, with the latter being purely imaginary. Thus, a calibrated measurement ratio M* can be defined as:

$$M^* = \frac{\text{Im}\left(\frac{V/I}{V_{air}/I_{air}}\right)}{\text{Abs}\left(\frac{V/I}{V_{air}/I_{air}}\right)} \quad (16)$$

The calibrated measurement ratio M* is advantageous because the ratio M* becomes insensitive to biases due to the measuring arrangement realization. The biases are typically caused by the number of turns in the coils and effect of metallic parts, such as metallic sleeves and the measuring arrangement body. However, the calibrated measurement ratio M* does not compensate for variations of the air or casing measurement due to temperature, pressure, and drift in the electronic arrangement.

Figure 3:
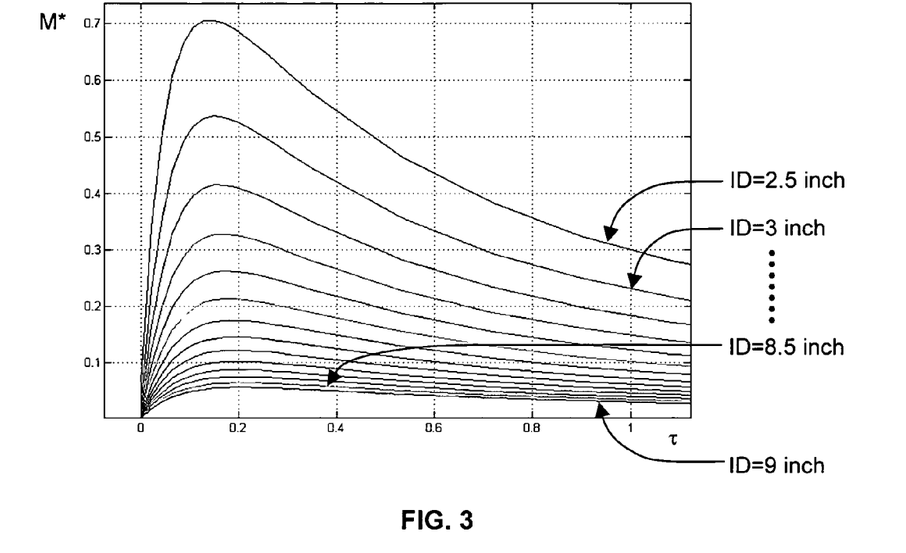
FIG. 3 illustrates the modeling results of the calibrated measurement ratio M* as a function of the real and dimensionless variable τ for various inner diameters of the casing.

FIG. 3 illustrates the modeling results of the calibrated measurement ratio M* as a function of the real and dimensionless variable τ. The real and dimensionless variable τ is depicted varying between zero and one. A set of curves has been calculated for various inner diameters ID of the casing ranging from 2.5 inch to 9 inch with a step of 0.5 inch.

In this example, the coils spacing L is 3 inch, and the first and second coil radius are the same $b_1=b_2=b=0.75$ inch.

When the real and dimensionless variable τ is very small compared to one, the measurement ratio M* approaches zero with a slope depending only on the ratio between the casing inside radius a and the coil radius b, namely a/b.

When the real and dimensionless variable τ is large, the measurement also tends towards zero. In this region the expansion of the dimensionless quantity T in the real and dimensionless variable τ begins to be inadequate since the value of $|k_2|d$ approaches unity. As a result, the casing wall thickness d influences the measurement.

Between those limiting cases, there exists a critical interval (e.g. around τ=0.2) that shows good sensitivity to both the ratio between the casing inside radius a and the coil radius b, namely a/b and the real and dimensionless variable τ. The inner diameter ID (ID=2a) of the casing clearly affects the overall amplitude of the measurement while the real and dimensionless variable τ affects the "shape" of the curves.

The method for measuring the physical parameters of the casing according to the invention will be explained hereinafter.

A plurality of voltage measurements $[V_1, V_2, \ldots V_n]$ and current measurements $[I_1, I_2, \ldots I_n]$ are performed at a plurality of frequencies $[f_1, f_2, \ldots f_n]$. Then a calibrated measurement ratio vector $M^*=[M^*_1, M^*_2, \ldots M^*_n]$ is calculated as hereinbefore described. The frequency vector corresponds to a vector of the real and dimensionless variable τ $[\tau_1, \tau_2, \ldots \tau_n]$, with the following scaling relation:

$$[\tau_1, \tau_2, \ldots \tau_n] = \tau_0 \sqrt{f_0} \left[\frac{1}{\sqrt{f_1}}, \frac{1}{\sqrt{f_2}}, \ldots \frac{1}{\sqrt{f_n}}\right] \quad (17)$$

It is assumed that during the logging proceeding, the measuring arrangement motion relative to the casing is sufficiently slow, such that the n measurements are performed according to substantially the same diameter ID of the casing and the same the ratio of magnetic permeability to electrical conductivity $\mu_2/\sigma_2$ nearby the transmitter and receiver coils. It is to be noted that the frequency $f_0$ can be chosen arbitrarily.

For example, the transimpedance may be measured with a current excitation having a frequency sweeping an interval of approximately 400 Hz to 16 kHz. The receiver coil and the transmitter coil may be separated by 3 inch. Each coil may have 550 turns of gauge AWG30 wire, a winding length of 0.25 inch and a mean winding radius of 0.75 inch. In this example, the receiver voltage measurements are typically of the order of 0.02 V to 0.04 V, and the current measurements are typically of the order of 0.001 A to 0.1 A.

Subsequently, a vectorial prediction function G is calculated for the measured quantity M*. The vectorial prediction function G is a function of the real and dimensionless variable τ and of the inner diameter ID for the desired parameter range of casing, namely:

$$[G_1, G_2, \ldots G_n]=G(ID, [\tau_1, \tau_2, \ldots \tau_n]) \quad (18)$$

The prediction function depends on the determined measuring arrangement geometry, namely the transmitter coil radius $b_1$, the receiver coil radius $b_2$, the distance between the coil L, and the finite size of coils.

Finally, a minimization algorithm is applied onto the vectorial prediction function G and the calibrated measurement ratio vector M*.

The objective of the minimization algorithm is to find the closest correspondence between the measurements (i.e. the calibrated measurement ratio vector M*) and the vectorial prediction function G by an appropriate choice of the inner diameter ID of the casing and the scaling of the real and dimensionless variable τ:

$$(\tau_0^*, ID^*) = \underset{\tau, ID}{\text{Min}} \left\| [M_1^*, M_2^*, \ldots M_n^*] - G\left(ID, \tau\sqrt{f_0}\left[\frac{1}{\sqrt{f_1}}, \frac{1}{\sqrt{f_2}}, \ldots \frac{1}{\sqrt{f_n}}\right]\right) \right\|^2 \quad (19)$$

The minimization algorithm may be any known minimization algorithms. For example, the minimization algorithm may advantageously be the Levenberg-Marquardt minimization algorithm.

The inner diameter ID and the ratio of magnetic permeability to electrical conductivity $\mu_2/\sigma_2$ can be readily extracted based on the solution of the above mentioned minimization step. This solution corresponds to the Maximum A Posteriori (MAP) solution for the calibrated measurement ratio vector M*.

Figure 4:
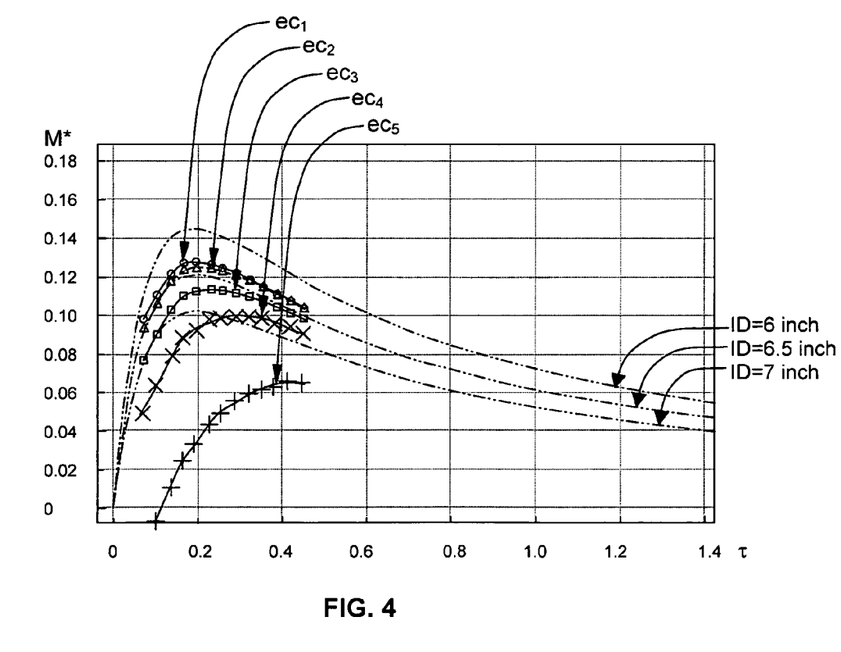
FIG. 4 illustrates a practical example wherein various measurements are compared to theoretical curves.

FIG. 4 illustrates a practical example wherein various measurements are compared to theoretical curves. The measurements have been performed within a casing having an inner diameter of 6.4 inch, at several frequencies scanning the range of the real and dimensionless variable τ between 0.05 and 0.45. Three theoretical curves corresponding to a first, a second and a third inner diameter ID of 6 inch, 6.5 inch and 7 inch, respectively are shown in FIG. 4.

FIG. 4 also illustrates the sensitivity of the measurements to measuring arrangement eccentricity relatively to the casing central axis Ax.

The first measured curve $ec_1$ (each circle corresponds to a measurement) corresponds to an eccentricity of zero.

The second measured curve $ec_2$ (each triangle corresponds a measurement) corresponds to an eccentricity of 10 mm±5 mm.

The third measured curve $ec_3$ (each square corresponds to a measurement) corresponds to an eccentricity of 20 mm±5 mm.

The fourth measured curve $ec_4$ (each cross corresponds to a measurement) corresponds to an eccentricity of 30 mm±5 mm.

The fifth measured curve $ec_5$ (each plus corresponds to a measurement) corresponds to an eccentricity of 40 mm±5 mm.

There is a good agreement between the measurement of less than 10 mm eccentricity and the theoretical curves.

Further, the calibrated measurement ratio M* appears to be sufficiently insensitive to an eccentricity of less than about 10 mm±5 mm.

Figure 5:
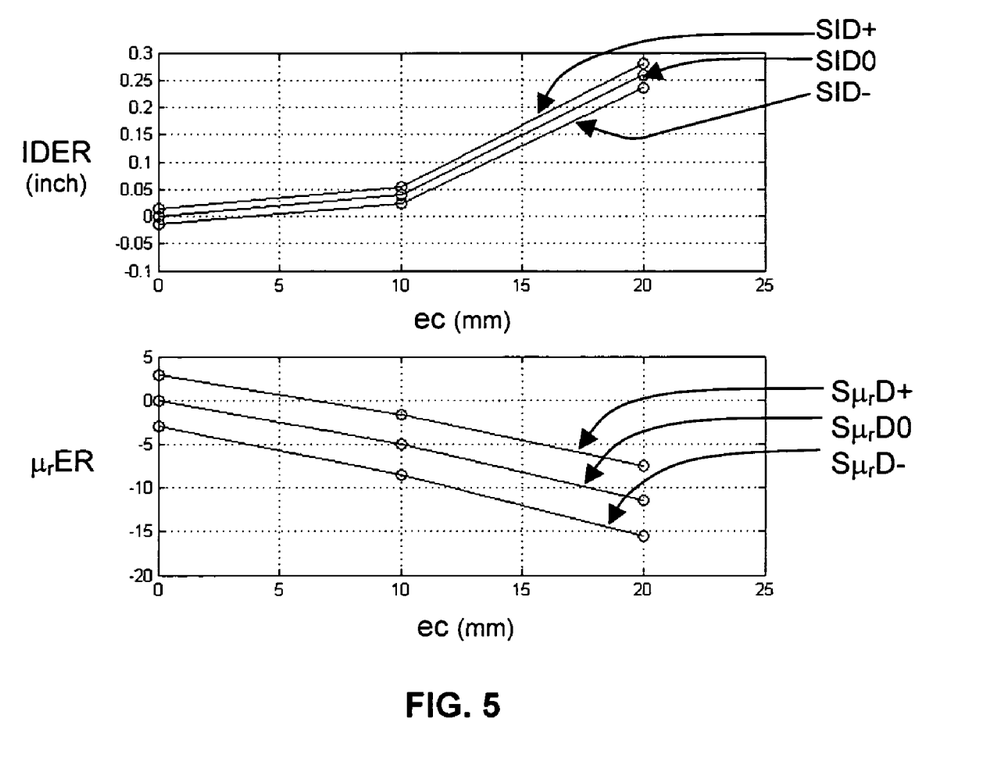
FIG. 5 illustrates the bias and the standard deviation for casing inner diameter (top of FIG. 5) and for relative permeability $\mu_r$ (bottom of FIG. 5) as a function of eccentricity.

FIG. 5 (top part) illustrates the bias and the standard deviation IDER of the measured casing inner diameter as a function of the eccentricity ec. The bias is the difference between the true casing inner diameter and the measured casing inner diameter.

The curve SID0 corresponds to the mean bias of the measurements of the casing inner diameter as a function of the eccentricity ec. The curve SID+ corresponds to the measurement error represented by one standard deviation above the mean bias curve SID0. The curve SID− corresponds to the measurement error represented by one standard deviation below the curve mean bias SID0.

FIG. 5 (bottom part) illustrates the bias and the standard deviation $\mu_r$ER of the relative permeability $\mu_r = \mu_2/\mu_0$ as a function of the eccentricity ec. The bias is the difference between true relative permeability $\mu_r = \mu_2/\mu_0$ and measured relative permeability.

The curve $S\mu_r D0$ corresponds to the mean bias of the measurements of the relative permeability as a function of the eccentricity ec. The curve $S\mu_r D+$ corresponds to the measurement error represented by one standard deviation above the curve $S\mu_r D0$. The curve $S\mu_r D-$ corresponds to the measurement error represented by one standard deviation below the curve $S\mu_r D0$.

FIG. 5 takes into consideration a casing conductivity $\sigma_2$ of $5 \times 10^6$ S/m, $\mu_0$ is the permeability of vacuum, the mean value of the inner diameter ID of the casing is 6.4 inch, and the mean value of the relative permeability $\mu_r$ is 70.

The error of the estimated inner diameter ID of the casing and of the real and dimensionless variable $\tau$ has been estimated through repeated measurements at a fixed eccentricity and with varying frequencies. By picking randomly three frequencies from among the set of measurements, a distribution of measurements was generated. Then, for each triplet of frequencies a vector ($\tau$, ID) was extracted. Further, an analysis of the solutions variability leads to an estimation of the measurement accuracy.

If eccentricity ec is maintained at less than 10 mm, the measurement uncertainty of the inner diameter ID of the casing remains under an acceptable level, namely ±0.05 inch. The relative permeability $\mu_r$ is measured with a confidence of ±10 units SI.

FINAL REMARKS

A particular application of the invention relating to applications in the oilfield industry has been described. However, the invention is also applicable to other type of industry where inspection of pipe is of interest, for example utility industry, chemical industry, etc. . . .

Finally, in the hereinbefore description, the transimpedance between a transmitter coil and a separate receiver coil has been measured. However, it will be apparent for a person skilled in the art that the invention is also applicable to the measurement of the impedance of a single coil.

The drawings and their description hereinbefore illustrate rather than limit the invention. Any reference sign in a claim should not be construed as limiting the claim. The word "comprising" does not exclude the presence of other elements than those listed in a claim. The word "a" or "an" preceding an element does not exclude the presence of a plurality of such element.

The invention claimed is:

1. A method for electromagnetically measuring physical parameters of a pipe (CS) by means of a measuring arrangement comprising a transmitter coil and a receiver coil, both coils being coaxial to and longitudinally spaced from each other, the measuring arrangement being adapted to be positioned into the pipe and displaced through the pipe, the pipe physical parameters being the pipe inner diameter (ID) and the pipe ratio of magnetic permeability to electrical conductivity ($\mu_2/\sigma_2$), the method comprising the steps of:
   a1) exciting the transmitter coil by means of a transmitter current ($I_i$), the transmitter current having a first excitation frequency ($f_1$),
   a2) measuring a receiver voltage ($V_i$) at the receiver coil,
   a3) determining a transimpedance ($V_i/I_i$) between the transmitter coil and the receiver coil based on the transmitter current ($I_i$) and the receiver voltage ($V_i$), and determining a measurement ratio ($M_i$) based on said transimpedance, wherein the method further comprises the steps of:
   b) repeating the excitation step a1), the measuring step a2), the transimpedance and the measurement ratio determination step a3) for at least a second excitation frequency ($f_2$) so as to define a measurement ratio vector ([$M_1$, $M_2$, . . . $M_n$]),
   c) calculating a prediction function vector ([$G_1$, $G_2$, . . . $G_n$]) based on the first frequency and at least the second excitation frequency, a plurality of potential pipe ratios of magnetic permeability to electrical conductivity and a plurality of potential pipe inner diameters, and
   d) applying a minimizing algorithm onto the measurement ratio vector ([$M_1$, $M_2$, . . . $M_n$]) and the prediction function vector ([$G_1$, $G_2$, . . . $G_n$]) and determining the pipe inner diameter (ID) and the pipe ratio of magnetic permeability to electrical conductivity ($\mu_2/\sigma_2$) corresponding to a maximum solution of the algorithm.

2. A method for electromagnetically measuring physical parameters of a pipe according to claim 1, wherein the measurement ratio ($M_i$) is determined by calculating the ratio between a real component of the transimpedance (Re[$V_i/I_i$]) and an absolute value of the transimpedance (Abs[$V_i/I_i$]).

3. A method for electromagnetically measuring physical parameters of a pipe according to claim 1, wherein the method further comprises the step of performing an air-calibration, and the measurement ratio ($M_i$) is a calibrated measurement ratio ($M_i^*$) determined by calculating the ratio between an imaginary component of an air normalized transimpedance (Im[($V_i/I_i$)/($V_{air}/I_{air}$)]) and an absolute value of the air normalized transimpedance (Abs [($V_i/I_i$)/($V_{air}/I_{air}$)]).

4. A method for electromagnetically measuring physical parameters of a pipe according to claim 1, wherein the prediction function vector ([$G_1$, $G_2$, . . . $G_n$]) is calculated for a determined measuring arrangement geometry ($b_1$, $b_2$, L) based on a real and dimensionless variable vector ([$\tau_1$, $\tau_2$, . . . $\tau_n$]) proportional to a plurality of potential pipe ratios of magnetic permeability to electrical conductivity and a normalized inverse of the square root of the first frequency and at least the second excitation frequency $$\left(\tau_0 \sqrt{f_0} \left[\frac{1}{\sqrt{f_1}}, \frac{1}{\sqrt{f_2}}, \dots \frac{1}{\sqrt{f_n}}\right]\right).$$

and a plurality of potential pipe inner diameters.

5. A method for electromagnetically measuring physical parameters of a pipe according to claim 1, wherein the minimizing algorithm is a Levenberg-Marquardt minimizing algorithm.

6. A logging tool (TL) for electromagnetically measuring physical parameters of a pipe (CS), the pipe physical parameters being the pipe inner diameter (ID) and the pipe ratio of magnetic permeability to electrical conductivity ($\mu_2/\sigma_2$), the logging tool being adapted to be positioned into the pipe, displaced through the pipe and coupled to a surface equipment (SE), the logging tool comprising a measuring arrangement and an electronic arrangement (EA) connected to the measuring arrangement, the measuring arrangement comprising a transmitter coil and a receiver coil, both coils being coaxial to and longitudinally spaced from each other, the electronic arrangement (EA) comprising a transmitter circuit (TXC) for exciting the transmitter coil by means of a transmitter current ($I_t$) according to a plurality of excitation frequencies, and a receiver circuit (RXC) for measuring a receiver voltage ($V_i$) at the receiver coil, wherein the electronic arrangement (EA) further comprises a processing circuit (PRO) for:
- determining a transimpedance ($V_i/I_t$) between the transmitter coil and the receiver coil based on the transmitter current ($I_t$) and the receiver voltage ($V_i$) for the plurality of excitation frequencies,
- determining a measurement ratio vector ($[M_1, M_2, \dots M_n]$) based on said transimpedance for the plurality of excitation frequencies,
- calculating a prediction function vector ($[G_1, G_2, \dots G_n]$) based on the plurality of excitation frequencies, a plurality of potential pipe ratios of magnetic permeability to electrical conductivity and a plurality of potential pipe inner diameters, and
- applying a minimizing algorithm onto the measurement ratio vector ($[M_1, M_2, \dots M_n]$) and the prediction function vector ($[G_1, G_2, \dots G_n]$) and determining the pipe inner diameter (ID) and the pipe ratio of magnetic permeability to electrical conductivity ($\mu_2/\sigma_2$) corresponding to a maximum solution of the algorithm.

* * * * *